United States Patent [19]
Harding

[11] Patent Number: 5,889,060
[45] Date of Patent: Mar. 30, 1999

[54] THERAPEUTIC USE OF(R)-VERAPAMIL FOR TREATING ANGINA

[75] Inventor: Deborah Phyllis Harding, Cambridge, United Kingdom

[73] Assignee: Darwin Discovery Limited, United Kingdom

[21] Appl. No.: 907,152

[22] Filed: Aug. 6, 1997

[30] Foreign Application Priority Data

Aug. 6, 1996 [GB] United Kingdom ................. 9616549.3

[51] Int. Cl.⁶ .................................................. A61K 31/35
[52] U.S. Cl. ............................................................ 514/654
[58] Field of Search ............................................. 514/654

[56] References Cited

U.S. PATENT DOCUMENTS 5,457,224  10/1995  Ehrmann et al. ........................ 558/354

FOREIGN PATENT DOCUMENTS

9 /50950   4/1995   WIPO .

OTHER PUBLICATIONS

Rakel,"Conn's Current Therapy", pp. 205–208. 1992.
Raschack, M., and K. Engelmann (1983) "Calcium Antagonistic Activity and Myocardial Ischemic Protection by Both Stereoismers of Verapamil" Adv. Miocardiol. vol. 4, pp. 505–512.
Chiba, S. et al. (1978) "Effects of Optical Isomers of Verapamil on SA Nodal Pacemaker Activity and Contractilcity of the Isolated Dog Heart" JPN. Heart J. 19(3):409–414.
Rabkin, S.W. 91994) "Verapamil Has Antiarryhthmic Effects That are mediated in Brain Through Endogenous Opioids" J. Cardiovac. Pharmacol. 23(5):814–821.
Thandroyen, F.T., et al. (1986) "The Influence of Verapamil and its Isomers on Vulnerability to Ventricular Fibrillation During Acute Myocardial Ischemia and Adrenergic Stimulation in Isolated Rat Heart" J. Mol. Cell. Cardiol. vol. 18, pp. 645–649.
Raschack, M. (1976) "Relationship of Antiarrhythmic to Inotropic Actibity and Antiarrhythimic Qualities of the Optical Isomers of Verapamil" Nauyn–Schmiedeberg's Arch. Pharmacol. 294, 285–291.
Curtis, M. J., M.J.A. Walker (1986) "The Calcium Antagonist Potency Ratio of the Optical Enatiomers of Verapamil in a Variety of Preparations" Proc. West. Pharmacol. Soc. 29:295–297.
Curtis, M.J., M.J.A. Walker (1986) "The Mechanism of Action of the Optical Enatiomers of Verapamil Against Ischaemis–Induced Arrhythimias in the Conscious Rat" br. J. Pharmac. 89, 137–147.

Berkow, R., and A.J. fletcher (eds.) (19920 "Diseases of the Heart and Pericardium" in The Merck Manual of Diagnosis and Therapy, 16th edition, published by Merck Research Laboratories, pp. 474–477.
Nayler, W. G. and W.J. Struuock (19830 "an Inhibitory Effect of Verapamil and Diltiazen on the Resease of Noradrenaline from Ischaemic and Reperfused Hearts" J. Mol. Cell. Cardiol. 16:331–334.
Arita, Makoto, and Tatsuto Kiyosue (1983) "*Modification of Depressed Fast channel Dependent Slow Conduction* by Lidocaine and Verapamil in the Presence of Absence of Catecholamines Evidence for Alteration of Preferential Ionic Chanels for Slow Conduction" Japanese Circulation Journal 47:68–80.
Arita, Makoto, et al. (1983) "Nature of Residual Fast Channel Dependent Action Potentials and Slow Conduction in Guinea Pig Ventricular Muscle and Its Modification by Isoproterenol" The American Journal of Cardiology, 51:1433–1440.
Watanabe, Hidehiko, et al. (1981) "Effects of Imipramine on Frequency–Force Relationship in Isolated Right Atrial Muscle of the Dog" Japan. J. Pharmacol. 31:289–291.
Surakitbanharn, Yosyong, et al. (1995) "Self–Association of Dexverapamil in Aqueous Solution"*Journal of Pharmaceutical Sciences*, 84(6):720–723.
Motzer, Robert, et al. (1995) "Phase I/II Trial of Dexverapamil Plus Vinblastine for Patients with Advanced Renal Cell Carcinoma" Journal of Oncology, 13(8):1958–1965.
Satoh, Keisuke,m et al. (1980) "Coronary Vasodilator and Cardiac Effects of Optical Isomers of Verapamil in the Dog" Journal of Cardiovascular Pharmacology 2:309–318.
Simamora, et al. (1994) "Compatibility Studies of Intravenous Dexverapamil Formulations" Pharmaceuticals Research, 11 910):S277 abstract.
Van Meel, J.C.A., et al. (1983) "Differential inhibition of $a_x$–adrenoceptor–mediated pressor responses by (+) –and (–) –verapamil in pithed rats" Journal Phamacol. 35:500–504.
Longstreth, James A. "Verapamil: A Chiral Challenge to the Pharmacokinetic and Pharmcodynamic Assessment of Bioavailability and Bioequivalence"(1984).

Primary Examiner—Raymond Henley, III
Attorney, Agent, or Firm—Saliwanchik, Lloyd & Saliwanchik

[57] ABSTRACT

(R)-verapamil, or a pharmaceutically-acceptable salt thereof, is useful in the treatment of angina.

3 Claims, No Drawings

THERAPEUTIC USE OF (R)-VERAPAMIL FOR TREATING ANGINA

FIELD OF THE INVENTION

This invention relates to the use of verapamil in the treatment of angina.

BACKGROUND TO THE INVENTION

Angina is a common indication of myocardial ischaemia either as a result of coronary artery disease or post acute myocardial infraction.

Verapamil (1) is presently in clinical use for the treatment of angina as a racemate.

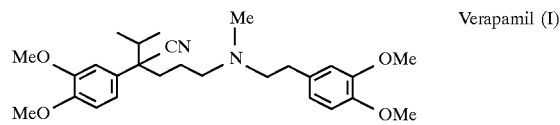

The opposite enantiomers of verapamil have different biological activities and different potencies. The pharmacological profile is determined by stereoselectivity of pharmacodynamics and pharmacokinetics.

Satoh et al, Journal of Cardiovascular Pharmacology (1980) 2:309–318 disclose details of a study of the vasodilatory and cardiodepressant effects of the two enantiomers of verapamil. The authors report that a equieffective doses in terms of increasing coronary sinus outflow, (R)-verapamil is significantly less cardiodepressant than (S)-verapamil. They conclude from this that (R)-verapamil may provide a safer means of treating angina than (S)-verapamil, but add that it is not known which of the enantiomers of verapamil is of grater therapeutic value in the treatment of angina.

In reaching this conclusion the authors considered only two properties of verapamil, namely decrease in myocardial oxygen consumption and increase in coronary blood flow. The reduction in oxygen consumption was attributed to the negative inotropic action and negative chronotropic and hypotensive effects. The authors considered that the coronary vasodilator effect was most important for the anti-anginal action of verapamil, and cited nifedipine as a coronary vasodilator with a virtual lack of cardiodepressant action. However, coronary vasodilation is just one possible component, and certainly not the most important component, of the mechanism of treatment of angina. Accordingly, several compounds tried in the treatment of angina on the basis of their coronary vasodilatory action alone have failed in the clinic. This illustrates that the model utilised in the study by Satoh et al is not a true angina model. Accordingly, no reliance can be given to any conclusion based on that study.

Curtis et al. Proc. West. Pharmacol. Soc. (1986) 29:295–297 describe the use of a pithed rat preparation to evaluate the peripheral vasodilatory potencies of the different enantiomers of verapamil. Their study illustrated a potency difference of 23-fold in favour of (S)-verapamil as compared to (R)-verapamil. In a conscious rat model, however, they found a potency difference of 4-fold, again in favour of (S)-verapamil, for lowering blood pressure. This data is, in its own right, confusing, and when viewed alongside the data reported by Satoh et al, it is very difficult to predict the overall vasodilatory profile of (R)-verapamil, and accordingly whether it will have any meaningful therapeutic activity in the treatment of angina.

Consequently, it is not known which, if either, of the enantiomers of verapamil will be effective in the treatment of angina in the clinic.

A target profile of once a day therapy giving 24 hour control and protection from the symptoms of angina is sought, without the undesirable, dose-limiting side effects experienced with the racemate, eg. depression of myocardial contractility (see Satoh et al) and atrioventricular (AV) conduction block (see Raschack, Naunyn-Schmiedeberg's Arch. Pharmacol. (1976) 294:285–291).

SUMMARY OF THE INVENTION

Surprisingly, it has now been found that (R)-verapamil significantly suppresses the increase in ventricular filling pressure which occurs during ischaemia, and which is one of the principal components of the transient myocardial failure characteristic of an anginal attack. It is believed that this is a result of a venodilatory effect associated with (R)-verapamil, which, coupled to its known arterial vasodilatory effect, will bear directly on the anti-anginal activity of this enantiomer.

This finding is based on data from a study which closely mimics angina in a clinical situation, and which shows, surprisingly, that at as little as, or less than, twice the dose of verapamil racemate, (R)-verapamil gave at least an equivalent, and significant, reduction in ischaemia-induced measures of angina, including left ventricular end-diastolic pressure. Thereby, (R)-verapamil may be useful in treatment of angina, and may be administered in higher amounts than currently used with the racemate, without the adverse effects normally associated with higher drug doses and which are reported to be associated with (S)-verapamil (see Satoh et al and Raschack, above).

DESCRIPTION OF THE INVENTION

The (R)-verapamil that is used in the present invention is substantially free of (S)-verapamil, eg. in an enantiomeric excess of at least 70%, preferably at least 95% excess, or higher. The (R)-verapamil may be substantially enantiopure. It may be used in the form of any suitable salt, eg. the hydrochloride.

There is an indication that (R)-verapamil is more slowly metabolised by the liver than (S)-verapamil, and therefore it may not be necessary to administer (R)-verapamil at twice the dose of the racemate to achieve a similar therapeutic effect; see Longstreth, J. A. Clin. Pharmacol. (1993) 18(2nd Edition): 315–336.

Administration of (R)-verapamil may be by any of the conventional routes, for instance oral, intravenous, sublingual, topical and rectal. Conventional formulations may verapamil will be formulated for oral administration. Typically, a suitable dosage of the active component is up to 500 mg per day, but any of the standard dosages for the racemate may be used, as given in the Monthly Index of Medical Specialities, published by Haymarket Press. These parameters are, however, given for guidance only, and will depend on the usual considerations, such as the age, weight etc. of the patient, as are within the skill of the attending physician.

The data on which the present invention is based are summarised below.

Myocardial ischaemia was induced in four sets of 6 to 8 anaesthetised mongrel dogs, of either sex, and having a body weight in excess of 17 kg, by complete occlusion of the anterior descending branch of the left coronary artery (LAD) in the presence of critical constriction of the circumflex coronary artery. The methodology used was in principle that described by Vegh et al, Europ. J. Pharmacol. (1987) 144:15–27.

The four test groups were as follows:

Group 1 (vehicle control)-1 ml saline was given as a rapid bolus injection, followed by intravenous saline infusion of 1 ml min$^{-1}$ over a period of 30 min.

Group 2-racemic verapamil was given in a total dose of 0.15 mg kg$^{-1}$. First, a bolus injection of 0.1 mg kg$^{-1}$ was given, followed by intravenous infusion of 0.05 mg kg$^{-1}$ over 30 min.

Group 3-(S)-verapamil was given in a total dose of 0.075 mg kg$^{-1}$. First, a bolus injection of 0.05 mg kg$^{-1}$ was given, followed by intravenous infusion of 0.025 mg kg$^{-1}$ over 30 min.

Group 4-(R)-verapamil was given in a total dose of 0.3 mg kg$^{-1}$. First, a bolus injection of 0.2 mg kg$^{-1}$ was given, followed by intravenous infusion of 0.1 mg kg$^{-1}$ over 30 min.

Amongst the measurements taken were the standard ischaemic parameters epicardial ST-segment elevation and inhomogeneity of electrical activation, over a period of 5 minutes in the area supplied by the LAD coronary artery. Changes in left ventricular pressure were also measured, including left ventricular end-diastolic pressure (LVEDP). Mean values of the data obtained are given in Table 1 below.

TABLE 1

|  | Dose | Reductions in Ischaemia - induced increases | | |
| --- | --- | --- | --- | --- |
|  |  | LVEDP mm Hg | Inhomogeneity msec. | ST-elevation mV |
| Control | Saline | 0.3 | −10 | −0.6 |
| Racemate | 0.15 mg kg$^{-1}$ | 12.4 | 74 | 5.4 |
| (R)-verapamil | 0.30 mg kg$^{-1}$ | 13.0 | 88 | 8.6 |
| (S)-verapamil | 0.075 mg kg$^{-1}$ | 13.0 | 93 | 6.8 |

The data obtained illustrate that all three drugs (the racemate and the separate enantiomers) have the ability to suppress ischaemic changes in a model relevant to the clinical situation. In particular, the increase in filling pressure, inhomogeneity and ST-elevation that occurred during ischaemia were all markedly reduced by verapamil in each of its forms.

Consequently, it is believed that (R)-verapamil may provide an effective treatment for angina, and at the same time a safer treatment, due to removal of the cardiodepressant effects and AV conduction block reported to be associated with (S)-verapamil.

I claim:

1. A method for treating angina, where said method comprises the administration of an effective amount of (R)-verapamil wherein said (R)-verapamil is substantially free of (S)-verapamil.

2. The method, according to claim 1, wherein said (R)-verapamil is administered orally.

3. The method, according to claim 1, wherein said (R)-verapamil is in an enantiomeric excess of at least 70%.

* * * * *

UNITED STATES PATENT AND TRADEMARK OFFICE
CERTIFICATE OF CORRECTION

PATENT NO. : 5,889,060

DATED : March 30, 1999

INVENTOR(S) : Deborah Phyllis Harding

It is certified that error appears in the above-identified patent and that said Letters Patent is hereby corrected as shown below:

*In the Claims*

Column 4, line 26: "where said" should read --wherein said--.

Signed and Sealed this

Twenty-fourth Day of August, 1999

Attest:

Q. TODD DICKINSON

*Attesting Officer*  *Acting Commissioner of Patents and Trademarks*